United States Patent [19]

Satake et al.

[11] Patent Number: 5,236,847
[45] Date of Patent: Aug. 17, 1993

[54] METHOD FOR ANALYZING AMINO ACIDS AND APPARATUS THEREFOR

[75] Inventors: Hiroshi Satake; Yoshio Fujii; Kohta Kimiyoshi, all of Katsuta, Japan

[73] Assignees: Hitachi, Ltd., Tokyo; Hitachi Instrument Engineering Co., Ltd., Ibaraki, both of Japan

[21] Appl. No.: 797,942

[22] Filed: Nov. 26, 1991

[30] Foreign Application Priority Data

Nov. 28, 1990 [JP] Japan .................................. 2-327659

[51] Int. Cl.$^5$ ...................... B01D 15/08; G01N 30/32
[52] U.S. Cl. ......................................... 436/89; 436/86; 436/90; 436/161; 436/178; 210/656; 210/635; 210/198.2; 422/70
[58] Field of Search ........................ 436/86, 87, 89, 90, 436/161, 171, 177, 178; 210/656, 635, 101, 198.2; 422/70

[56] References Cited

U.S. PATENT DOCUMENTS 4,133,753 1/1979 Takeuchi .......................... 260/112.5

OTHER PUBLICATIONS

Willard, Hobart. "Liquid Column Chromotography." *Instrumental Methods of Analysis.* 6th ed. New York: D. Van Nostrand Co., 1981.

Primary Examiner—James C. Housel
Assistant Examiner—David Redding
Attorney, Agent, or Firm—Antonelli, Terry, Stout & Kraus

[57] ABSTRACT

A method for analyzing amino acids in biological liquids wherein a buffer liquid including unknown components to be analyzed is introduced to a separation column for separating amino acids. After reaction of the buffer liquid in a reactor, the amino acids are detected by a photometer. The flow rate of the buffer liquid is maintained at a predetermined value until the asparagine, glutamine acid and glutamine are separated from the separation column and the flow rate of the buffer liquid is varied stepwise or in linear gradient after separation of the above three components from the separation column.

4 Claims, 6 Drawing Sheets

FIG. 7

| STEP (30) | TIME (min) (31) | BUFFER (TOTAL 100%) (32) ||||| COLUMN TEMP (33) | FLOW P1 (34) | RATE (ml/min) P2  P3 (35) |
|---|---|---|---|---|---|---|---|---|---|
|   |   | V1 | V2 | V3 | V4 | V5 |   |   |   |
| 1 | 0.0 | 100 | — | — | — | — | 38 | 0.20 | 0.40  0.00 |
| 2 | 9.0 | — | — | — | — | — | 31 |   |   |
| 3 | 34.9 | 100 | — | — | — | — |   |   |   |
| 4 | 35.0 | 80 | 20 | — | — | — |   |   |   |
| 5 | 38.5 | — | — | — | — | — | 58 |   |   |
| 6 | 52.0 | — | — | — | — | — |   | 0.44 |   |
| 7 | 55.0 | 70 | 30 | — | — | — |   |   |   |
| 8 | 55.1 | 10 | 90 | — | — | — |   |   |   |
| 9 | 57.5 | — | — | — | — | — | 40 |   |   |
| 10 | 64.5 | 10 | 90 | — | — | — |   |   |   |
| 11 | 64.6 | — | 100 | — | — | — |   |   |   |
| 12 | 69.0 | — | 100 | — | — | — | 70 |   |   |
| 13 | 69.1 | — | — | 100 | — | — |   |   |   |
| 14 | 83.5 | — | — | 100 | — | — | 45 |   |   |
| 15 | 84.5 | — | — | — | 100 | — |   |   |   |
| 16 | 97.0 | — | — | — | 100 | — | 70 |   |   |
| 17 | 103.0 | — | — | — | — | 100 |   |   |   |
| 18 | 116.0 | — | — | — | — | 100 |   |   |   |
| 19 | 116.1 | — | — | — | — | — |   |   |   |
| 20 | 123.0 | 100 | — | — | — | — |   |   |   |
| 21 | 123.1 | — | — | — | — | — | 38 |   |   |
| 22 | 145.0 | — | — | — | — | — |   |   |   |
| 23 | 160.0 | 100 | — | — | — | — |   | 0.20 |   |

METHOD FOR ANALYZING AMINO ACIDS AND APPARATUS THEREFOR

BACKGROUND OF THE INVENTION

The present invention relates to a method for analyzing amino acids of a biological liquid and an apparatus therefor.

In an apparatus for analyzing amino acids included in biological liquids, for example, urine and blood serum, efforts for improving separation performance of three components, asparagine, glutamine acid and glutamine, have been continued as disclosed in Japanese Laid-open Patent Publication Sho-59-10,849(1984) and U.S. Pat. No. 4,133,735. In separating about forty amino acid components in the biological liquids, in order to improve the separation performance of the three components which are most important and most difficult to be separated, some analysis method have been proposed, for example, refinement of filler (ion exchange resin) in the separation column, improvement of buffer liquid composition used as separation liquids, and change of the temperature of the separation column. However, every method can not satisfy the requirements completely.

FIGS. 1 and 2 are chromatograms of a mixed reference liquid corresponding to biological liquids including the following forty-two amino acids.

TABLE

| | Names of amino acids |
|---|---|
| C1 | phosphoserine |
| C2 | taurine |
| C3 | urea |
| C4 | aspartic acid |
| C5 | hydroxyproline |
| C6 | threonine |
| C7 | serine |
| C8 | asparagine |
| C9 | glutamic acid |
| C10 | glutamine |
| C11 | sarcosine |
| C12 | α-amino adipic acid |
| C13 | proline |
| C14 | glycine |
| C15 | alanine |
| C16 | citrulline |
| C17 | α-amino-n-butyric acid |
| C18 | valine |
| C19 | cysteine |
| C20 | methionine |
| C21 | d,l-cystathionine |
| C22 | ios-leucine |
| C23 | leucine |
| C24 | nor-leucine |
| C25 | tyrosine |
| C26 | phenylalanine |
| C27 | β-alanine |
| C28 | β-amino-iso-butyric acid |
| C29 | homoscysteine |
| C30 | γ-amino-iso-butyric acid |
| C31 | tryptophan |
| C32 | ethanolamine |
| C33 | ammonia |
| C34 | d,l-hydroxylysine |
| C35 | ornithine |
| C36 | histidine |
| C37 | 1-methylhistidine |
| C38 | lysine |
| C39 | 3-methylhistidine |
| C40 | anserine |
| C41 | carnosine |
| C42 | arginine |

The chromatogram shown in FIG. 1 is obtained by using a new separation column and the other one shown in FIG. 2 is obtained by using an old separation column which has been used in the measurement of about five hundred blood serum samples.

In FIG. 1, peaks indicative of asparagine 21, glutamine acid 22, and glutamine 23 are separated clearly. On the contrary, in FIG. 2, the asparagine 21a and the glutamine acid 22a are not clearly separated and a valley between the two peaks disappears. As a result, both the peaks are calculated as an one peak in the calculation process of the peak area and the apparatus decides that there is no peak indicative of the asparagine 21a.

When the above situation occurs, an operator makes a decision that there is no reliability of qualitative analysis and quantitative analysis on all components because of termination of available time period and changes the separation column to a new one. The frequent exchange of the separation column makes running cost of the analysis up, and therefor, extension of the available time has been desired.

SUMMARY OF THE INVENTION

The object of the present invention is to provide a method for analyzing amino acids and apparatus therefor having well balanced separation performance to the components of the liquids to be analyzed.

As a result of detail examination on FIGS. 1 and 2, inventors have found that components except the above three components are sufficiently separated and the separation column is available to the other components except the three components after measuring of five hundred samples. That is, (1) The analysis components which are impossible to be separate center in one part of the chromatogram, for example, the first one quarter of the whole analysis time period. On the other hand, decrease of the separation performance does not occurs in the remaining (the latter) three quarters of the analysis time period.

(2) It is easy to improve the separation performance of the components separated during the latter three quarters of the whole analysis time period described in the article (1).

(3) When the flow rate of the buffer liquid is decreased, the separation performance is improved through all the analysis time period.

The present invention is made on the basis of the above three facts and has following features.

A method for analyzing amino acids in biological liquids comprising introducing a buffer liquid including components to be analyzed to a separation column and separating amino acids, detecting the amino acids by a detector after reaction of the buffer liquid in a reactor, the flow rate of the buffer liquid is changed with respect to the analysis time during the analyzing process.

An amino acids analyzing apparatus comprising a buffer liquid, supplying means for the buffer liquid, sampler, a separation column disposed down stream of the sampler, a reaction device, detector, and means for changing the flow rate of the buffer liquid with respect to the retention time. The flow rate is changed stepwise or in linear and gradient.

With respect to the article (1) as shown in FIG. 2, three components which are most difficult to be separated, that is, asparagine 21a, glutamine acid 22a and glutamine 23a center in the first analysis time of 18 minutes to 23 minutes in the whole analysis time of 125 minutes. After 25 minutes from the beginning of the analyzing, the analysis of the three components is completed. The analysis time necessary for the three components is about first one fifth of whole analysis time.

On the other hand, the article (3) is realized by spending longer time in analysis, that is, for example, by decreasing the flow rate of the buffer liquid down to two third and decreasing the linear speed of the separation column.

As shown in FIG. 3, the asparagine 21b, glutamine acid 22b, glutamine 23b are sufficiently separated by extending the analysis time to one and half times as long as that of the FIG. 2.

The above described method is able to extend the available life time of the column. However, the method requires a long analysis time period (whole analysis time) and therefore, is inappropriate to apply a hospital routine work which has to analyze large number of samples.

FIG. 4 shows a chromatogram by an improved method. In the improved method, the analysis time of the tryptophane 24 is quickened by increasing the temperature of the separation column between the peaks indicative of the tryptophan 24 and ethanolamine 25 as shown in FIG. 4. Additionally, the separation performance is improved by changing the composition of the buffer liquid between the peaks indicative of ammonia 26 and hydroxylysine 27.

As it is possible to improve the separation performance by controlling of the temperature of separation column or composition of the buffer liquid without changing the flow rate of the buffer liquid in analyzing the components except three components of asparagine 21c, glutamine acid 22c, and glutamine 23c, the flow rate of the buffer liquid can be increased in the present invention.

As shown in FIG. 4, the total analysis time is shortened to 90 minutes by accelerating the flow rate of the buffer liquid up to 1.4 times as quick as that of the FIG. 1.

FIG. 5 is a chromatogram by the analyzing method having all features described in the above articles (1) to (3).

The analyzing process is divided into two groups on the basis of the article (1). The first group G1 includes the components from the beginning of the analysis to the α-amino adipic acid, and the second group G2 includes the components from proline to the last, arginine. In the analysis region of the group G1, the flow rate of the buffer liquid is decreased on the basis the feature described in the article (3). On the contrary, in the analysis region of the group 2, the flow rate of the buffer liquid is increased on the basis of the feature described in the article (2). In selecting a border between the groups G1 and G2 each having the different flow rate, it is preferable to decide a position on which adjacent two peaks indicative of the components to be analyzed are not close to each other.

Although the base line level changes in the time region 28 when the flow rate changes, the region has no peaks indicative of components and has no influence on an area calculation for the quantitative analysis.

As explained in the article (1), it is very important that the analysis time of the three components lies in about first one fifth of the analysis time. If the peaks indicative of the three components exist in the latter half of the analysis time, it is impossible to improve the separation performance by decreasing the flow rate in the latter half of the analysis time period from the viewpoint of the characteristics of the usual chromatography. Because the cause accelerating the separation starts from the beginning of the analysis process.

Therefore, only when in case the cause accelerating the separation exists in the first half of the analysis time period, effect of acceleration of the separation appears in the latter half of the separation time period. It is impossible to improve the separation performance even if the flow rate of the buffer liquid is changed without the preparation of the cause of the acceleration beforehand which accelerates the separation in the latter analysis time.

However, methods except change of the flow rate, for example, changing of the column temperature, PH of the buffer liquids, concentration of organic solvents, are effective.

To improve the separation performance of the three components, asparagine, glutamine acids, and glutamine, a method decreasing the flow rate of the buffer liquid as described above and a method decreasing the concentration of the lithium ion as shown in Japanese Laid-open Patent Publication Sho 59-10849 are most effective methods.

BRIEF DESCRIPTION OF THE DRAWINGS

FIG. 7 is an analysis program according to an embodiment of the present invention.

BRIEF DESCRIPTION OF THE PREFERRED EMBODIMENT

Figure 6:
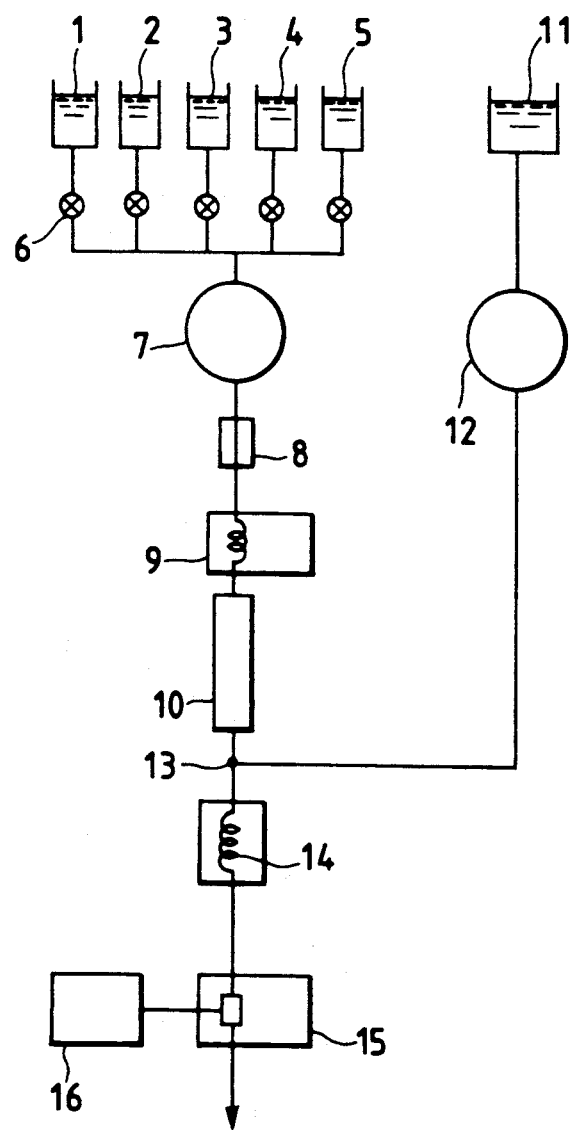
FIG. 6 is a schematic diagram explaining an amino acid analysis apparatus according to an embodiment of the present invention.

FIG. 6 is a schematic diagram explaining the flow route of an amino acids analyzing apparatus. One of buffer liquids 1 to 4 is selected by one of electro-magnetic valve series 6 and a column reproducing liquid 5 are supplied to a separation column 10 by a buffer pump 7 through an ammonia filter column 8 and an auto sampler 9. The amino acids separated by the separation column 10 are mixed with ninhydrin reagent 11 supplied by a ninhydrin pump 12 in a mixer 13 and transferred to a reaction coil 14 for reaction. Amino acids colored by the reaction are detected successively by a photometer 15 and the detection result is outputted by data processing unit 16 as a chromatogram.

In the above embodiment, Hitachi high speed amino acids analyzer Model L-8500 was used as a analyzing device. Commercial sold L-8500-PF-KIT produced by Mitsubishi Chemical Company was used as buffer liquids. Ninhydrin reagent liquid L-8500 Set produced by Wako Junyaku kougyou Co. Ltd. was used as a ninhydrin reagent. Packed Column 2622SC produced by Hitachi, Ltd. was used as a separation column.

FIG. 7 shows an example of an analysis program chart by the analysis method according to the present invention. Following step 30, analysis time 31 is recited.

According to the lapse of the analysis time, magnet valves V1 to V5 are changed over to select the buffer liquids one after another. In FIG. 7, reference numeral 100 means the fully open of the corresponding magnet valve and reference numerals 80 and 20 means 80% open and 20% open of the respective two valves, for example v1=80% open and V2=20% open in the time ratio. The column temperature 33 shows the temperature of the separation column 10. In the embodiment, the column temperature is started from 38° C. and controlled within the range of 31° C. to 70° C. to keep the separation condition best. Numeral 0.20 in the flow rate 34 means that the flow rate of the buffer liquid pump 7 is 0.20 ml/min.

Figure 1:
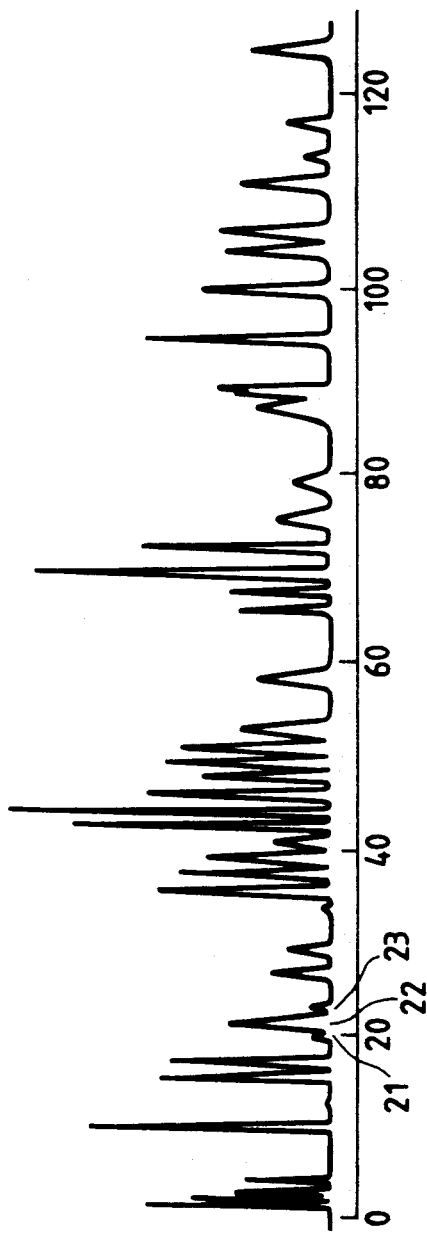
FIGS. 1 and 2 are chromatograms showing examples of analysis of amino acids in an biological liquid by a traditional amino acid analyzer.
Figure 2:
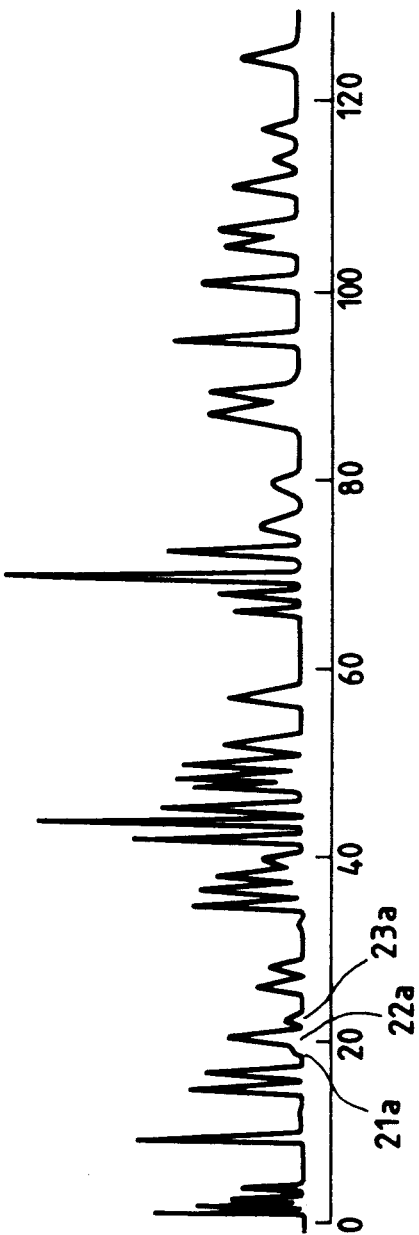
Figure 3:
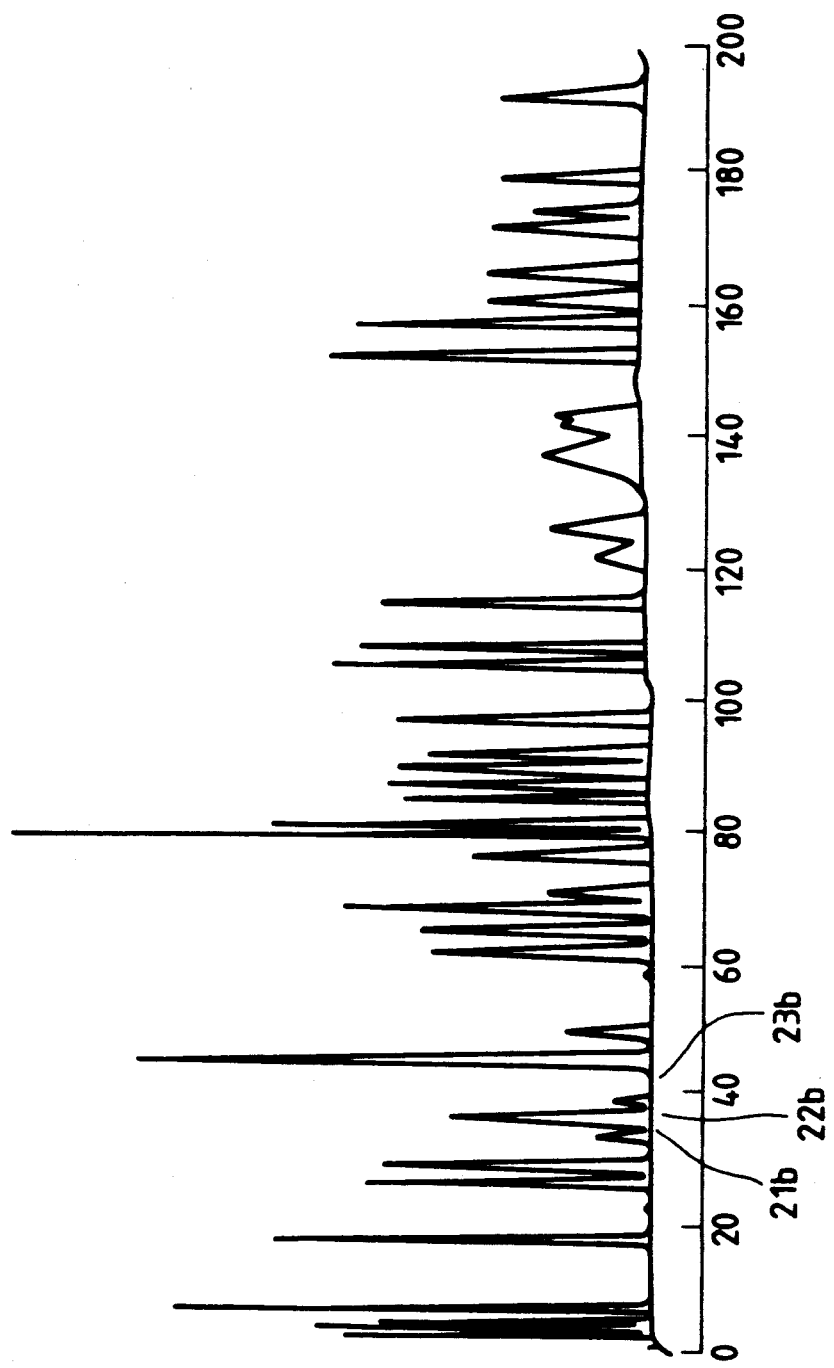
FIG. 3 is a chromatogram showing an example of analysis of amino acids in an biological liquid by an amino acid analyzer with high separation performance.
Figure 4:
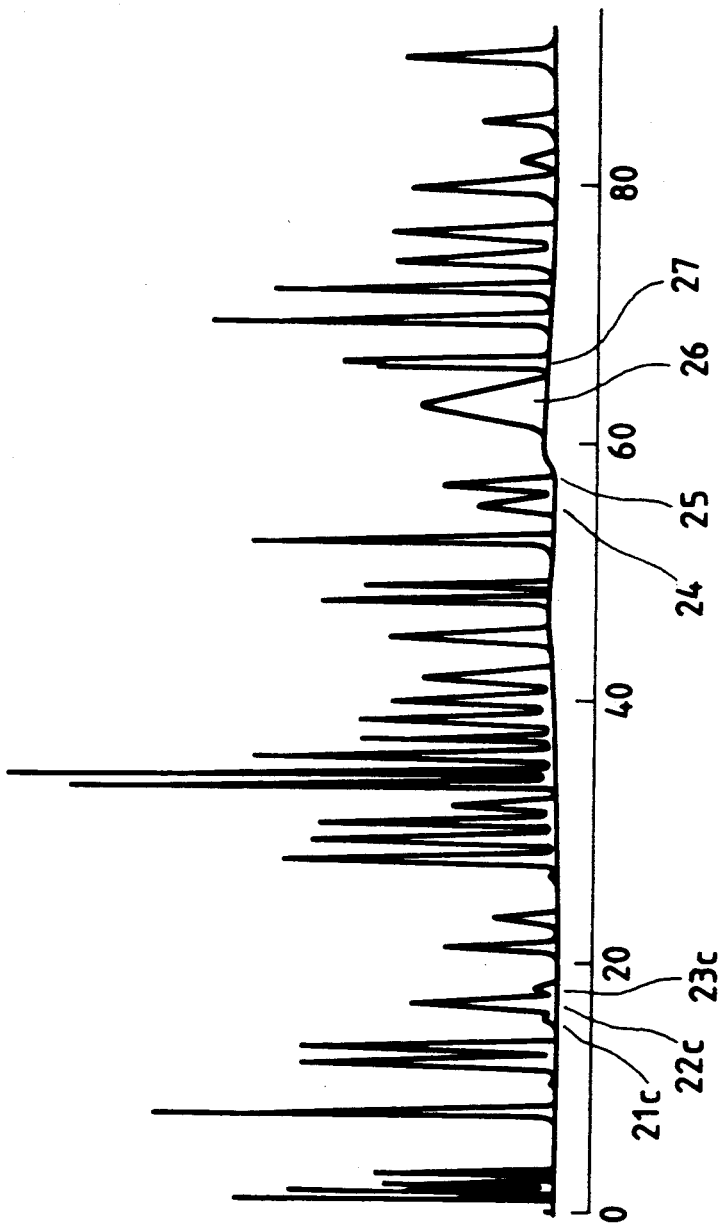
FIG. 4 is a chromatogram showing an example of high speed analysis of amino acids in an biological liquid.
Figure 5:
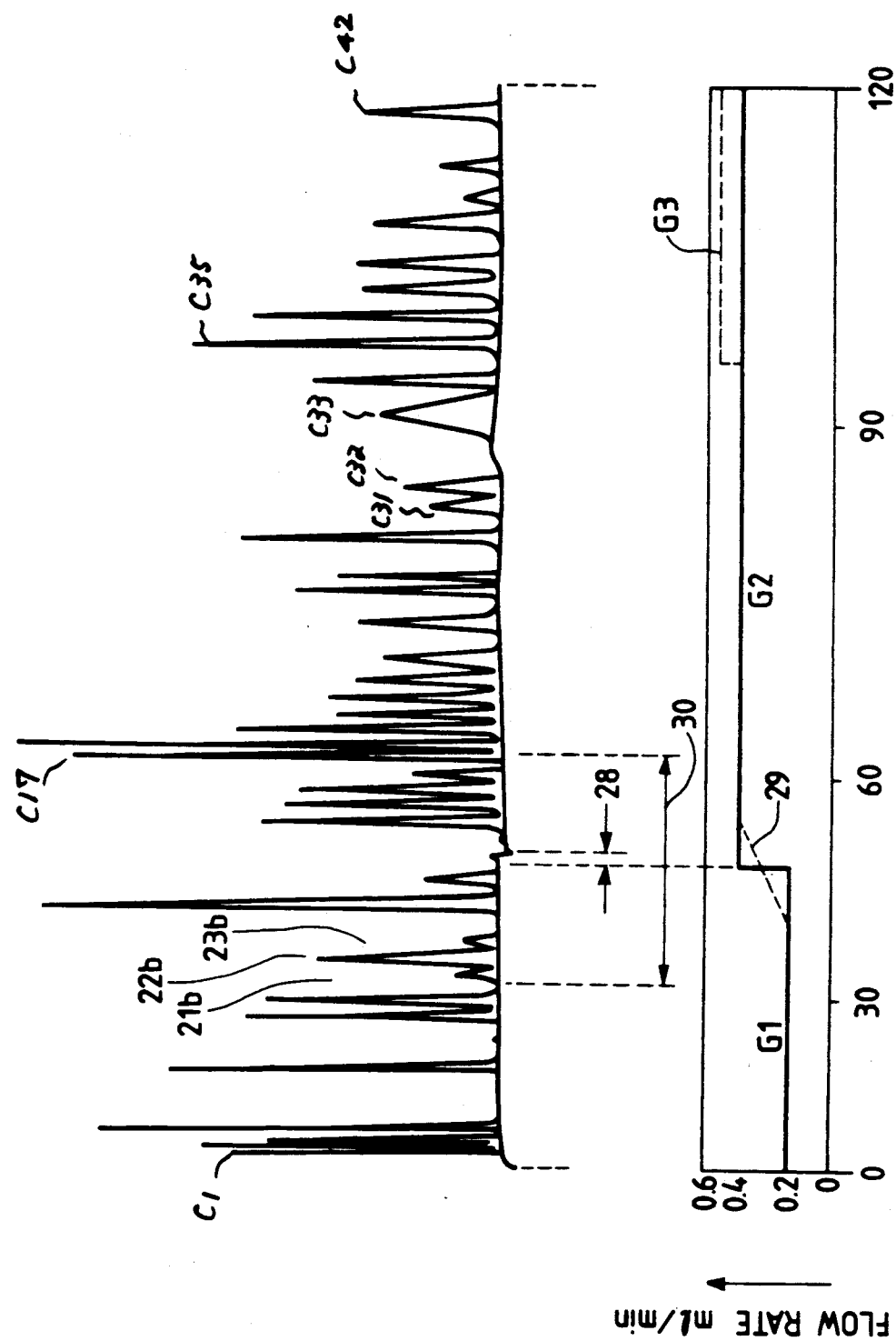
FIG. 5 is a chromatogram showing an example of analysis of amino acids in an biological liquid according to an embodiment of the present invention.

When the analyzing device is operated by the above described analysis program, a chromatogram is obtained as shown in FIG. 5. At the beginning, the buffer liquid is introduced slowly into the separation column at a flow rate of 0.20 ml/min and the components from phosphoserine C1 to α-amino adipic acid C2 are separated. Then, 52 minutes after, the flow rate of the buffer liquid is increased to 0.44 ml/min. in the latter half of the analysis time.

In the embodiment, the moving speed of the chart is also increased by a data processing device 16 to two times as quick as before according to twice increase of the speed of the buffer liquids. Most appropriate separation condition is selected by the change of a sort of the buffer liquid and the separation column temperature during the analysis.

According to the present embodiment, the whole analysis is completed in 120 minutes. Then, for next analysis, the operation for cleaning of the column and return to the original flow rate of the buffer liquid is carried out automatically.

By repeating the above operation, the analysis of large number of the samples is performed successively. According to the above embodiment, the following advantages are obtained.

(1) It is possible to separate three components of asparagine, glutamine acid and glutamine with high accuracy which are most difficult to be separated.

(2) By high accuracy separation of the above three components, separation unbalance among the whole components is removed and available life time period of the separation column is extendable by twice in comparison with the ordinary device.

(3) It is applicable to analyze a large number of sample because separation performance of the separating column is improved and analysis time period is not increased.

(4) The variation of the base line in the flow rate change region 28 as shown in FIG. 5 is lessened by change over smoothly as shown. See reference numeral 29.

(5) The flow rate change varies the reaction time and reaction rate by the change of the mixture rate with the ninhydrin. However, the accuracy of the quantitative analysis does not decrease in the amino acid analyzer because the calibration of the sample to be analyzed using wellknown sample(reference sample) is carried out before analysis.

In the embodiment, the flow rate of the buffer liquid is changed after 52 minutes from the start of the analysis, the time point of the flow rate change is able to be set variably according to the nature of the sample to be analyzed.

A flat portion of the base line between the glutamine 23b and sarcosine C11 is able to be changed into a sharp peak by changing the flow rate at the portion (about 41 minutes). No change over shocks appears on the base line if the flow rate change is executed by the gradient method of the present invention. Therefore, the change over region 30 can be positioned before the separation of the asparagine acid 21b as shown in FIG. 5. The suitable range is about 32 minutes to 62 minutes, that is, from the peak of asparagine acid to the peak of α-amino butyric acid C17 as shown in FIG. 5. Too late change over time point lengthens total analyzing time. Therefore, it is appropriate to set the change over time in consideration of the total analysis time. In the embodiment, the total analysis time is selected within two hours.

Generally speaking, the increase of the flow rate results in decrease of the separation performance of the peaks indicative of the components and increase of the load pressure of the separation column 10. Moreover, shortening of the reaction time decreases the height of the peaks (sensibility) and available time of the column. Therefore, it is not preferable to quicken extremely the flow rate of the buffer liquid.

The change over ratio of the flow rate is decided according to the degree of the separation performance of the peaks present in the region. If the sharpness of the peaks (theoretical stages) is reversely proportional to the flow rate, the change over rate is set in response to the separation performance of the required peak. In the same time, as the change over rate is related to the analysis time, it is preferable to set 0.1 to 0.3 for the first group and 0.2 to 0.6 for the second group G2.

In the embodiment, although the flow rate change is executed at only one position, if necessary, it is possible to execute the flow rate change at two or more positions. For example, the separation condition is very well between ornithine C35 and arginine C42 in FIG. 5. Therefore, it is possible to set a flow rate change position of group G3 before the ornithine, for example, 0.55 ml/min. By changing the flow rate, the analysis time is reduced to 20 minutes and the analysis time is reduced by 5 minutes as follows:

$$25(min.) \times 0.44/0.55 = 20(min.)$$

According to the present invention, it is possible to separate the three components of the asparagine, glutamine acid, and glutamine included in the biological liquid are separated completely with well balance with the other components in the separation performance. Therefore, it is possible to enlarge the available time of the separation column 2 times as long as that of the ordinary analysis device.

We claim:

1. A method for analyzing amino acids in biological liquids including asparagine, glutamine acid and glutamine comprising:
   adding a biological liquid sample also including unknown amino acid components to be analyzed to a buffer liquid;
   introducing the buffer liquid including the unknown components to be analyzed to a separation column and separating amino acids therein;
   detecting the separated amino acids by a detector; the flow rate of the buffer liquid being maintained at a predetermined value until asparagine, glutamine acid and glutamine are separated from the separation column and the flow rate of the buffer liquid is increased after detection of the asparagine, glutamine acid and glutamine separated from the separation column.

2. A method for analyzing amino acids in biological liquids according to claim 1, wherein said flow rate of the buffer liquid is increased stepwise.

3. A method for analyzing amino acids in biological liquids according to claim 1, wherein the flow rate of the buffer liquid is increased in linear gradient.

4. An amino acid analyzing apparatus comprising:

a source for supplying a buffer liquid;

a sampler for supplying a sample of biological liquid containing unknown amino acids and asparagine, glutamine acid and glutamine to the buffer liquid;

means for transferring the buffer liquid to the sampler, from the sampler with the sample to a separation column, through a reaction device to a detector;

said separation column disposed downstream of the sampler for separating amino acids therein;

said reaction device connected to the separation column for receiving separated amino acids and for reacting the separated amino acids with reagent;

said detector for detecting the reacted amino acids including means for detecting the asparagine, glutamine acid, and glutamine separated from said separation column; and means for maintaining the flow rate of the buffer liquid at a predetermined value until the asparagine, glutamine acid and glutamine are separated from the separation column and for increasing the flow rate of the buffer liquid after detection of the asparagine, glutamine acid and glutamine separated from the separation column.

* * * * *